(12) United States Patent
Imamura et al.

(10) Patent No.: US 9,629,608 B2
(45) Date of Patent: Apr. 25, 2017

(54) ULTRASOUND DIAGNOSIS APPARATUS AND CONTROL METHOD

(71) Applicant: Toshiba Medical Systems Corporation, Otawara-shi (JP)

(72) Inventors: Tomohisa Imamura, Nasushiobara (JP); Atsushi Sumi, Otawara (JP); Kuramitsu Nishihara, Otawara (JP); Naohisa Kamiyama, Utsunomiya (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 482 days.

(21) Appl. No.: 13/855,951

(22) Filed: Apr. 3, 2013

(65) Prior Publication Data
US 2013/0267852 A1 Oct. 10, 2013

(30) Foreign Application Priority Data

Apr. 5, 2012 (JP) ................................. 2012-086745
Mar. 7, 2013 (JP) ................................. 2013-045605

(51) Int. Cl.
*A61B 8/00* (2006.01)
*A61B 8/14* (2006.01)
*A61B 8/08* (2006.01)

(52) U.S. Cl.
CPC ............ *A61B 8/4461* (2013.01); *A61B 8/145* (2013.01); *A61B 8/4494* (2013.01); *A61B 8/483* (2013.01); *A61B 8/466* (2013.01); *A61B 8/488* (2013.01)

(58) Field of Classification Search
None
See application file for complete search history.

(56) References Cited

U.S. PATENT DOCUMENTS 5,090,414 A * 2/1992 Takano .................... 600/461
8,852,109 B2 10/2014 Yamagata
(Continued)

FOREIGN PATENT DOCUMENTS

| CN | 101491445 A | 7/2009 |
|----|-------------|--------|
| JP | 2004-506458 | 3/2004 |

(Continued)

OTHER PUBLICATIONS

Nikolov et al., "Practical Applications of Synthetic Aperture Imaging", Ultrasonics Symposium (IUS), IEEE, Oct. 11, 2010.*
(Continued)

*Primary Examiner* — Christopher Cook
(74) *Attorney, Agent, or Firm* — Oblon, McClelland, Maier & Neustadt, L.L.P.

(57) ABSTRACT

An ultrasound diagnosis apparatus of embodiments includes an ultrasound probe, a scanning controller, and a display controller. The ultrasound probe is configured to be capable of ultrasound three dimensional scanning by swinging a plurality of transducer elements in a direction orthogonal to the arrangement direction of the transducer elements. The scanning controller is configured to control the ultrasound probe to scan a plurality of intersecting cross sections while swinging the transducer elements. The display controller is configured to control such that a plurality of ultrasound images based on ultrasound scanning performed on the cross sections are displayed on a given display.

13 Claims, 13 Drawing Sheets

(56) References Cited

U.S. PATENT DOCUMENTS

| | | | | |
|---|---|---|---|---|
| 2005/0124880 A1* | 6/2005 | Shinomura | .............. | A61B 8/13 600/437 |
| 2011/0310228 A1* | 12/2011 | Yao | ........................ | A61B 8/466 348/46 |
| 2012/0059260 A1* | 3/2012 | Robinson | ............. | A61B 8/0841 600/439 |
| 2012/0165679 A1* | 6/2012 | Orome et al. | ................ | 600/461 |

FOREIGN PATENT DOCUMENTS

| | | |
|---|---|---|
| JP | 2006-204621 | 8/2006 |
| JP | 2006-231035 | 9/2006 |
| JP | 2007-512068 | 5/2007 |

OTHER PUBLICATIONS

Combined Chinese Office Action and Search Report issued Sep. 9, 2014 in Patent Application No. 201310118085.9 (with English translation of categories of cited documents).
Office Action issued Jan. 17, 2017, in Japanese Patent Application 2013-045605.

* cited by examiner

SWING DIRECTION

PUNCTURE GUIDE
ATTACHMENT POSITION

ULTRASOUND DIAGNOSIS APPARATUS AND CONTROL METHOD

CROSS-REFERENCE TO RELATED APPLICATIONS

This application is based upon and claims the benefit of priority from Japanese Patent Application No. 2012-086745, filed on Apr. 5, 2012; and Japanese Patent Application No. 2013-045605, filed on Mar. 7, 2013, the entire contents of all of which are incorporated herein by reference.

FIELD

Embodiments described herein relate generally to an ultrasound diagnosis apparatus and a control method.

BACKGROUND

Conventionally, there is known an ultrasound diagnosis apparatus capable of collecting three dimensional data (volume data) using a mechanical four dimensional probe. Whether a region to be observed is included in three dimensional space scanned by the mechanical four dimensional probe is normally determined based on display of an ultrasound image of one cross section that is generated by scanning the cross section with the mechanical four dimensional probe. However, it is difficult to simply refer to the ultrasound image of one cross section and accurately determine whether the entire region to be observed is included in the three dimensional ultrasound scanning area.

Alternatively, in order to determine whether the region to be observed is included in the three dimensional ultrasound scanning area of the mechanical four dimensional probe, the ultrasound diagnosis apparatus generates and displays, based on the collected volume data, a plurality of desired cross sections, such as a multi planar reconstruction (MPR) image on orthogonal two cross sections or orthogonal three cross sections. However, it is necessary to scan the whole of three dimensional space using the mechanical four dimensional probe to generate and display a plurality of desired cross sections based on the volume data. Thus, a frame rate and scanning density of ultrasound beams cannot be increased.

DETAILED DESCRIPTION

An ultrasound diagnosis apparatus of embodiments includes an ultrasound probe, a scanning controller, and a display controller. The ultrasound probe is configured to be capable of ultrasound three dimensional scanning by swinging a plurality of transducer elements in a direction orthogonal to the arrangement direction of the transducer elements. The scanning controller is configured to control the ultrasound probe to scan a plurality of intersecting cross sections while swinging the transducer elements. The display controller is configured to control such that a plurality of ultrasound images based on ultrasound scanning performed on the cross sections are displayed on a given display.

The following describes embodiments of an ultrasound diagnosis apparatus in detail with reference to the accompanying drawings.

Figure 1:
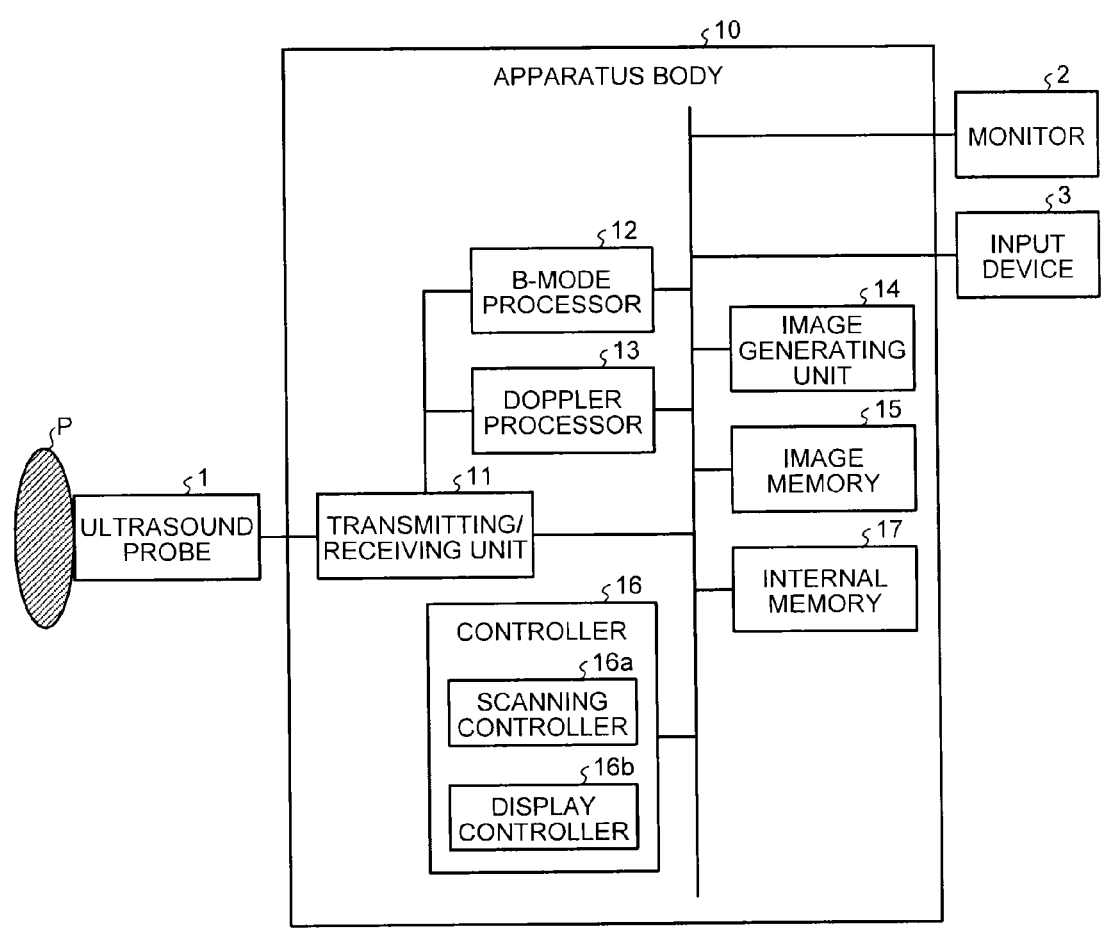
FIG. 1 is a block diagram of a configuration example of an ultrasound diagnosis apparatus according to a first embodiment.

Described first is the configuration of an ultrasound diagnosis apparatus according to a first embodiment. FIG. 1 is a block diagram of a configuration example of the ultrasound diagnosis apparatus in the first embodiment. As exemplified in FIG. 1, the ultrasound diagnosis apparatus includes an ultrasound probe 1, a monitor 2, an input device 3, and an apparatus body 10.

The ultrasound probe 1 includes a plurality of transducer elements. The transducer elements generate ultrasound waves based on driving signals supplied from a transmitting/receiving unit 11 included in the apparatus body 10, which is described later. The transducer elements of the ultrasound probe 1 are piezoelectric transducer elements, for example. The ultrasound probe 1 receives reflected wave signals from a subject P, and converts them into electrical signals. The ultrasound probe 1 also includes aligning layers provided on the piezoelectric transducer elements, backing materials for preventing backward propagation of ultrasound waves from the piezoelectric transducer element, etc. The ultrasound probe 1 is connected to the apparatus body 10 in an attachable manner.

When the ultrasound probe 1 transmits ultrasound waves to the subject P, the transmitted ultrasound waves are sequentially reflected on the discontinuity surfaces of acoustic impedance in the tissues of the subject P, and are received as reflected wave signals by the piezoelectric transducer elements of the ultrasound probe 1. The amplitude of the received reflected wave signals depends on difference between the acoustic impedances of the discontinuity surfaces on which ultrasound waves are reflected. The reflected wave signals obtained when transmitted ultrasound pulses are reflected on the surfaces of flowing blood, a moving heart wall, etc. are subjected to a frequency shift by the Doppler effect depending on the speed component of a moving entity regarding an ultrasound wave transmission direction.

Figure 2:
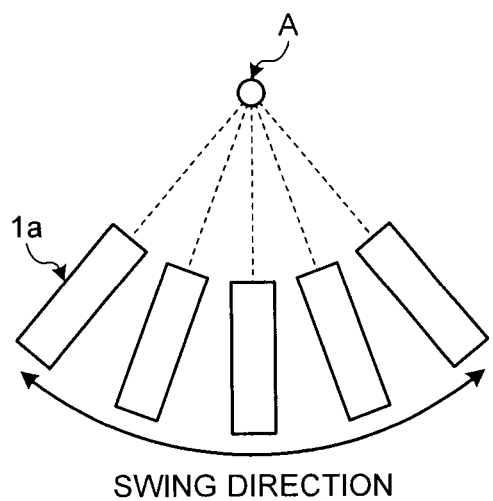
FIGS. 2, 3, and 4 are diagrams for explaining an ultrasound diagnosis probe in the first embodiment.
Figure 3:
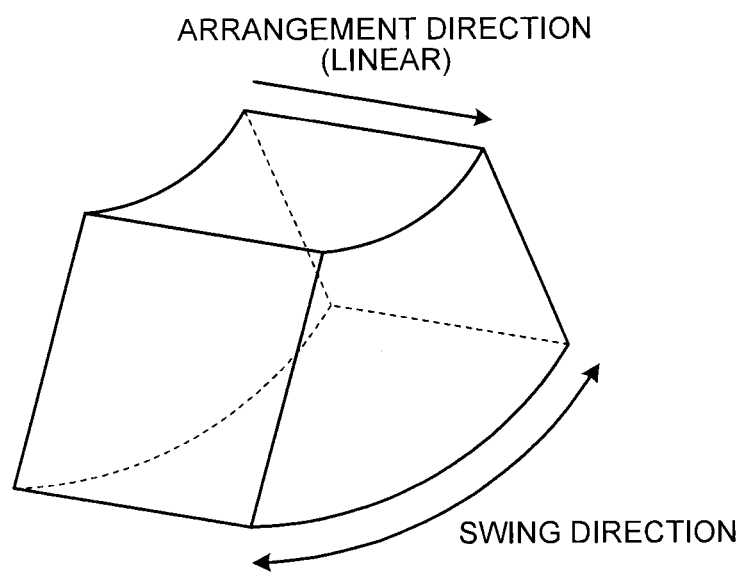
Figure 4:
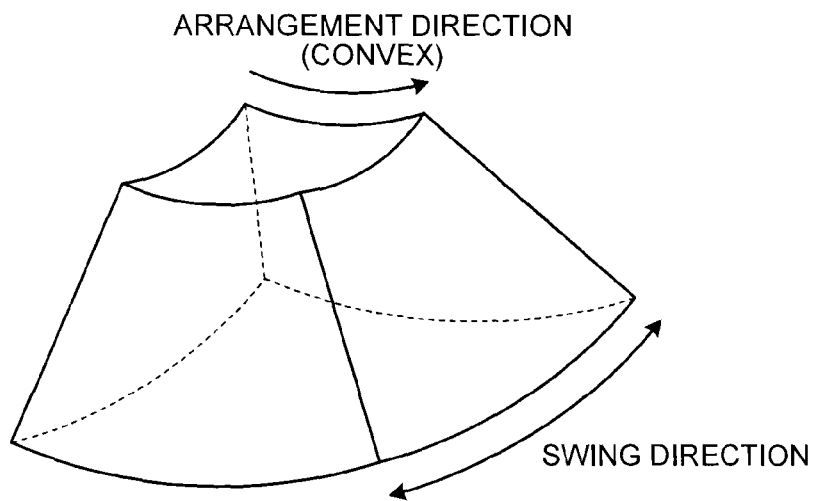

Here, the ultrasound diagnosis apparatus in the first embodiment includes a mechanical four dimensional probe as the ultrasound probe 1 that is capable of ultrasound three dimensional scanning by swinging transducer elements in a direction orthogonal to the arrangement direction of the transducer elements. FIGS. 2 to 4 are diagrams for explaining the ultrasound probe in the first embodiment.

Concretely, the ultrasound probe 1 that is a mechanical four dimensional probe performs ultrasound three dimensional scanning using a transducer element array 1a including a plurality of arranged transducer elements being swung around a swing axis A, as illustrated in FIG. 2. That is, the respective transducer elements constituting the transducer element array 1a perform ultrasound transmission/reception sequentially along an arrangement direction, for example, whereby the ultrasound probe 1 performs ultrasound two dimensional scanning. Then, the transducer elements transmit and receive ultrasound waves in a state that the transducer element array 1a is swung around the swing axis A, whereby the ultrasound probe 1 can scan the subject P three-dimensionally. The ultrasound probe 1 can perform ultrasound scanning on a two dimensional cross section when the position of the transducer element array 1a is fixed. The ultrasound three dimensional scanning by the ultrasound probe 1 may be performed in a manner that transducer elements perform ultrasound transmission/reception while the transducer element array 1a is swinging, or in a manner that ultrasound scanning on a two dimensional cross section is performed several times at a plurality of positions in a swing direction at which the transducer element array 1a is fixed.

The cross section exemplified in FIG. 2 is a cross section that passes the swing axis A and is vertical to the arrangement direction of the transducer element array 1a. As illustrated in FIG. 2, the transducer element array 1a is swung around the swing axis A, and thus the swing direction has a curvature depending on a distance between the transducer element array 1a and the swing axis A. An angle in a swing direction (swing angle) and swing speed are changed under the control of the transmitting/receiving unit 11 through a scanning controller 16a, which is described later.

The ultrasound probe 1 that is the mechanical four dimensional probe performs ultrasound transmission/reception in a given three dimensional space by a single swing of the transducer element array 1a along the swing direction having the curvature exemplified in FIG. 2. First, the ultrasound probe 1 performs ultrasound transmission/reception in three dimensional space once in a going stroke in the swing direction, and then ultrasound transmission/reception in three dimensional space once in a returning stroke in the swing direction. The ultrasound diagnosis apparatus in the first embodiment includes the ultrasound probe 1 capable of ultrasound three dimensional scanning in chronological order by repeating reciprocation of the transducer element array 1a in the swing direction.

Here, when a plurality of transducer elements constituting the transducer element array 1a are linearly arranged and the ultrasound probe 1 performs linear scanning, the three dimensional space to be scanned with ultrasound has a shape illustrated in FIG. 3, for example, because the arrangement direction of the transducer element array 1a is linear. In the shape exemplified in FIG. 3, a plane including the swing axis A and the arrangement direction is a rectangular, and a plane including the swing direction and being vertical to the arrangement direction is fan-shaped depending on the curvature of the swing direction.

When a plurality of transducer elements constituting the transducer element array 1a are arranged in a convex form toward an ultrasound wave transmission direction and the ultrasound probe 1 performs convex scanning, the three dimensional space to be scanned with ultrasound has a shape illustrated in FIG. 4, for example, because the arrangement direction of the transducer element array 1a also has a curvature. In the form exemplified in FIG. 4, a plane including the swing axis A and the arrangement direction is fan-shaped depending on the curvature of the arrangement direction, and a plane including the swing direction and being vertical to the arrangement direction is fan-shaped depending on the curvature of the swing direction.

The input device 3 is connected to the apparatus body 10, and includes a mouse, a keyboard, a button, a panel switch, a touch command screen, a foot switch, a trackball, etc. The input device 3 receives various setting requests from an operator of the ultrasound diagnosis apparatus, and transmits the received various setting requests to the apparatus body 10.

The input device 3 receives a request for starting three dimensional scanning with the ultrasound probe 1, or a request for starting two dimensional scanning with the ultrasound probe 1, for example.

The monitor 2 displays a graphical user interface (GUI) allowing the operator of the ultrasound diagnosis apparatus to input various setting requests through the input device 3, or displays ultrasound images generated by the apparatus body 10, for example. To be more specific, the monitor 2 displays in vivo morphologic information or blood flow information, as images, based on video signals input from an image generating unit 14, which is described later.

The apparatus body 10 generates an ultrasound image based on reflective wave signals received by the ultrasound probe 1. The apparatus body 10 includes the transmitting/receiving unit 11, a B-mode processor 12, a Doppler processor 13, an image generating unit 14, an image memory 15, a controller 16, and an internal memory 17, as exemplified in FIG. 1.

The transmitting/receiving unit 11 includes a pulse generator, a transmission delay unit, a pulsar, etc. and supplies driving signals to the ultrasound probe 1. The pulse generator repeatedly generates rate pulses for forming transmission ultrasound waves, at a given rate frequency. The transmission delay unit applies a delay time that is required to converge the ultrasound wave generated by the ultrasound probe 1 into the form of a beam and to determine transmission directionality and that corresponds to each of the piezoelectric transducer elements, to each of the rate pulses generated by the pulse generator. The pulsar applies driving signals (driving pulses) on the ultrasound probe 1 at timing based on the rate pulse. That is, the transmission delay unit changes a delay time provided to the rate pulses to arbitrarily adjust the transmission direction of ultrasound waves transmitted from the surfaces of the piezoelectric transducer elements.

The transmitting/receiving unit 11 has a function of changing instantaneously a transmission frequency, a transmission driving voltage, etc. so as to perform a given scanning sequence based on an instruction of the controller 16, which is described later. In particular, the change of the transmission driving voltage is implemented with a linear amplifier type transmission circuit capable of shifting the value instantaneously, or by a mechanism switching a plurality of power units electrically.

The transmitting/receiving unit 11 includes a preamplifier, an analog/digital (A/D) converter, a reception delay unit, an adder, etc., and performs various kinds of processing on reflected wave signals received by the ultrasound probe 1 to generate reflected wave data. The preamplifier amplifies the reflected wave signals for each channel. The A/D converter A/D-converts the amplified reflected wave signals. The reception delay unit provides a delay time necessary for determining reception directivity. The adder performs addition processing regarding the reflected wave signals processed by the reception delay unit to generate reflected wave data. Performing addition processing, the adder emphasizes reflected components from a direction depending on the reception directivity of the reflected wave signals, and forms a comprehensive beam for ultrasound transmission/reception based on the reception directivity and the transmission directivity.

The form of output signals from the transmitting/receiving unit 11 may be selected variously such as signals containing phase information referred to as radio frequency (RF) signals, and signals containing amplitude information obtained after envelope detection processing.

The B-mode processor 12 receives the reflected wave data from the transmitting/receiving unit 11, and performs logarithmic amplification, envelope detection processing, etc. on the reflected wave data to generate data representing signal intensity of each scanning line by brightness (B-mode data).

The Doppler processor 13 performs frequency analysis regarding velocity information, based on the reflected wave data received from the transmitting/receiving unit 11, and extracts the components of a blood flow, tissue, and a contrast agent echo by the Doppler effect. Thereafter the Doppler processor 13 generates Doppler data obtained by extracting blood flow information such as average velocity, variance, and power at a number of points on each scanning line.

The B-mode processor 12 and the Doppler processor 13 can process both two dimensional reflected wave data and three dimensional reflected wave data. That is, the B-mode processor 12 generates two dimensional B-mode data based on the two dimensional reflected wave data, and generates three dimensional B-mode data based on the three dimensional reflected wave data. The Doppler processor 13 generates two dimensional Doppler data based on the two dimensional reflected wave data, and generates three dimensional Doppler data based on the three dimensional reflected wave data.

The image generating unit 14 generates an ultrasound image based on the B-mode data generated by the B-mode processor 12 or the Doppler data generated by the Doppler processor 13, and stores the generated ultrasound image in the image memory 15 or the internal memory 17, both of which are described later.

To be more specific, the image generating unit 14 generates, based on the B-mode data, a B-mode image representing intensity of the reflected wave data by brightness. The image generating unit 14 generates, based on the Doppler data, a color Doppler image representing average velocity, variance, and the amount of blood flow, or combination thereof distinguishably by colors.

To be more specific, the image generating unit 14 converts (scan-converts) a plurality of scanning line signal arrays of ultrasound scanning into a scanning line signal array in a video format represented by a television, etc. to generate an ultrasound image (B-mode image or color Doppler image) as a display image. To be still more specific, the image generating unit 14 performs coordinate transformation in accordance with a form of ultrasound scanning by the ultrasound probe 1 to generate an ultrasound image for display. The image generating unit 14 performs interpolation processing to compensate lack data in the scanning line signal array after scanning conversion, and generates an ultrasound image for display.

Moreover, the image generating unit 14 performs coordinate transformation regarding the three dimensional B-mode data generated by the B-mode processor 12 to generate a three dimensional B-mode image. The image generating unit 14 also performs coordinate transformation regarding the three dimensional Doppler data generated by the Doppler processor 13 to generate a three dimensional color Doppler image. The image generating unit 14 also has a function of performing rendering processing on volume data such as three dimensional B-mode image and three dimensional color Doppler image in order to generate a two dimensional image for displaying the volume data on the monitor 2. The rendering processing by the image generating unit 14 includes processing of performing a multi planer reconstruction (MPR) to reconstruct an MPR image from the volume data. Alternatively, the rendering processing by the image generating unit 14 includes volume rendering processing for generating a two dimensional image reflecting three dimensional information (volume rendering image).

The image generating unit 14 synthesizes character information in association with various parameters, divisions, body marks, etc., with the ultrasound image. The image generating unit 14 includes therein a recording memory (not illustrated) storing image data, and the operator can retrieve images recorded during examination, after diagnosis, for example.

The image memory 15 is a memory storing data received from the B-mode processor 12 and the Doppler processor 13. The data stored in the image memory 15 can be retrieved by the operator after diagnosis, for example, and constitutes an ultrasound image for display through the image generating unit 14. The ultrasound image can be reproduced as a still image or as a movie with a plurality of images.

The image memory 15 can also store the ultrasound images generated by the image generating unit 14, etc. Such image data can be also retrieved by the operator from the image memory 15 after diagnosis, and thus reproduced as a still image or as video with a plurality of images.

The internal memory 17 stores control programs for ultrasound transmission/reception, image processing, and display processing, diagnosis information (patient identification (ID) and doctor's view, for example), and various kinds of data such as diagnosis protocols and various body marks. The internal memory 17 is also used to keep image data stored in the image memory 15, if necessary. Various kinds of data stored in the internal memory 17 can be transmitted to external peripherals through an interface (not illustrated).

The controller 16 is a control processor (central processing unit (CPU)) implementing a function as an information processing device (computer), and controls the entire processing in the ultrasound diagnosis apparatus. To be more specific, the controller 16 controls processing of the transmitting/receiving unit 11, the B-mode processor 12, the Doppler processor 13, and the image generating unit 14, based on various instructions or setting requests that are input by the operator through the input device 3, or programs and various kinds of setting information that are read out from the internal memory 17. The controller 16 also controls such that ultrasound images, etc. stored in the internal memory 17 or the image memory 15 are displayed on the monitor 2.

Here, the controller 16 in the first embodiment includes the scanning controller 16a and a display controller 16b, as exemplified in FIG. 1. The scanning controller 16a controls ultrasound scanning with the ultrasound probe 1 that is the mechanical four dimensional probe, through the transmitting/receiving unit 11. The display controller 16b controls the displaying of the ultrasound image on the monitor 2. The control processing of each of the scanning controller 16a and the display controller 16b in the first embodiment is described later in detail.

The entire configuration of the ultrasound diagnosis apparatus in the first embodiment is described above. In such a configuration, the ultrasound diagnosis apparatus in the first embodiment collects volume data with the ultrasound probe 1 that is the mechanical four dimensional probe. Here, whether a region to be observed is included in the three dimensional space scanned by the ultrasound probe 1 is conventionally determined by displaying an ultrasound image of one cross section that is generated by the image generating unit 14 when the ultrasound probe 1 scans the cross section. However, it is difficult to simply refer to the ultrasound image of one cross section and accurately determine whether the entire region to be observed is included in the three dimensional ultrasound scanning area. It is possible to use a bi-plane probe capable of scanning two cross sections in order to determine a position with which the mechanical four dimensional probe is brought into contact. However, in such a case, it is difficult for the operator to accurately rearrange the mechanical four dimensional probe at the contact position of the bi-plane probe that is determined optimum for his/her observation, thus deteriorating examination efficiency.

Alternatively, in order to determine whether the region to be observed is included in the three dimensional ultrasound scanning area by the mechanical four dimensional probe, the ultrasound diagnosis apparatus conventionally generates and displays, based on collected volume data, a plurality of desired cross sections, such as MPR images of orthogonal two cross sections or orthogonal three cross sections. However, it is necessary to scan the entire three dimensional space using the mechanical four dimensional probe to generate and display a plurality of desired cross sections. One-time swing of the ultrasound probe 1 takes about 10 seconds, for example, and thus a frame rate with which images for the determination are displayed is reduced. When the position of the ultrasound probe 1 is moved to determine whether a region to be observed is included, for example, the operator conventionally needs to wait for about 10 seconds until the image after the movement is updated and displayed. There is also a method of reducing scanning density of an ultrasound beam to improve the frame rate. However, in this case, the image quality of the ultrasound image is deteriorated.

Then, in the first embodiment, the following control is performed by the scanning controller 16a and the display controller 16b so as to display a high quality images for determining whether a region to be observed is included in the three dimensional area scanned by the mechanical four dimensional probe at a high frame rate.

The scanning controller 16a controls the ultrasound probe 1 to scan a plurality of intersecting cross sections while swinging the transducer elements. That is, the scanning controller 16a controls the transmitting/receiving unit 11 so that the ultrasound probe 1 scans intersecting cross sections while swinging transducer elements. In other words, the ultrasound scanning performed with the ultrasound probe 1 is controlled by the scanning controller 16a and the transmitting/receiving unit 11. The display controller 16b controls such that a plurality of ultrasound images based on ultrasound scanning on the cross sections are displayed on the monitor 2. In other words, the scanning controller 16a controls such that the ultrasound probe 1 scans a plurality of intersecting cross sections in the three dimensional space that can be scanned with ultrasound in order to generate an ultrasound image for display to be referred to by the operator for observation.

Here, the scanning controller 16a controls such that each of the cross sections is scanned at least once during one-time reciprocating swing of transducer elements. In other words, the scanning controller 16a controls such that one or more combinations of cross sections, among combinations of the intersecting cross sections, are scanned during one-time reciprocating swing of the transducer element array 1a, whereby all the cross sections are scanned at least once during the time.

Concretely, the scanning controller 16a controls such that at least one of cross sections is scanned during the one-time swing of the transducer elements. In other words, the scanning controller 16a controls such that reflected data for at least one frame is generated by the one-time swing. To be more specific, in the first embodiment, the scanning controller 16a controls the positions of the transducer elements performing ultrasound transmission/reception so that one part of cross sections is scanned once in the going stroke of swing and the rest of cross sections are scanned once in the returning stroke of swing.

Figure 5:
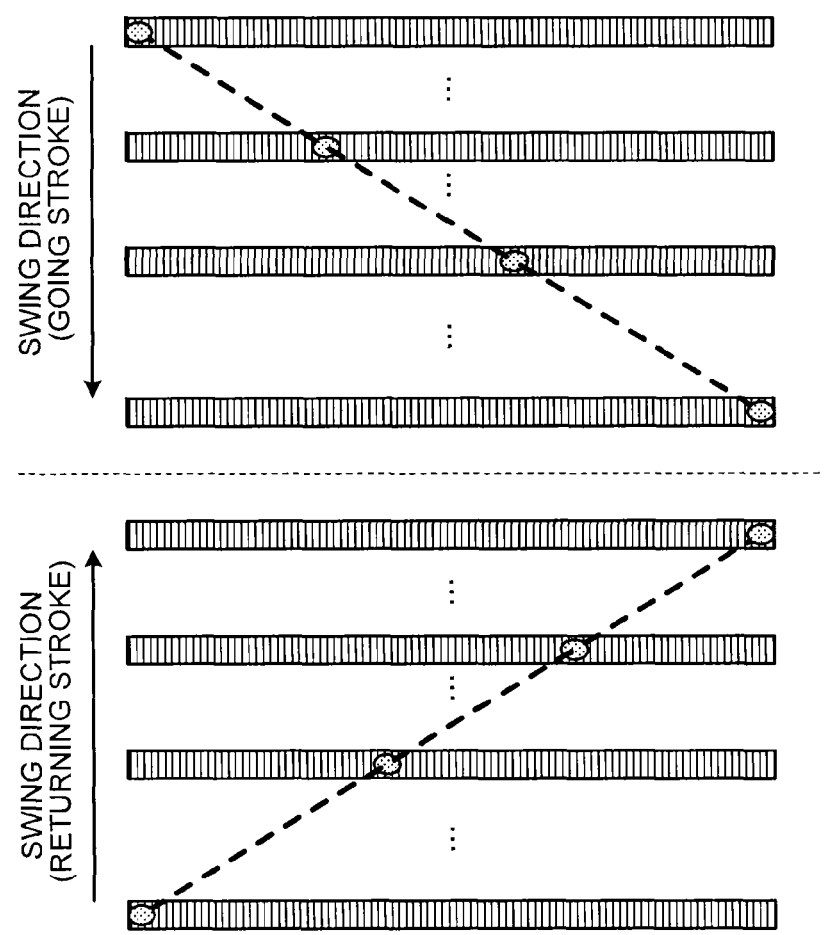
FIGS. 5, 6, and 7 are diagrams for explaining an example of scanning control by a scanning controller in the first embodiment.
Figure 6:
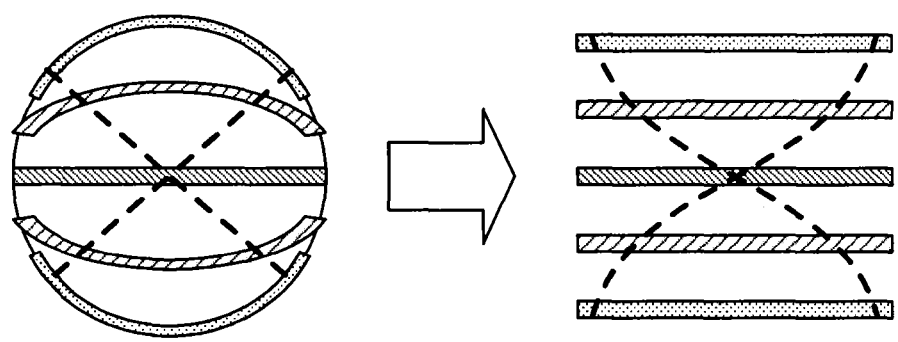
Figure 7:

For example, in the first embodiment, the scanning controller 16a scans two intersecting sections as a plurality of cross sections. In such a case, the scanning controller 16a shifts the transducer elements performing ultrasound transmission/reception from one end to the other end in one-time swing, and arranges a shifting direction of the transducer elements performing ultrasound transmission/reception to be the same in the going stroke and the returning stroke. FIGS. 5 to 7 are diagrams for explaining an example of scanning control by the scanning controller in the first embodiment. In FIG. 5, respective positions of the swinging transducer element array 1a are illustrated in rectangular shapes when the ultrasound probe 1 is viewed from above the contact face of the ultrasound probe 1 and the subject P.

The scanning controller 16a in the first embodiment controls such that the transducer elements performing ultrasound transmission/reception are sequentially shifted from the left end to the right end in the going stroke in the swing direction, as illustrated in the upper diagram of FIG. 5. Here, the scanning controller 16a controls such that the transducer element at the left end performs ultrasound transmission/reception when swing in the going stroke is started and the transducer element at the right end performs ultrasound transmission/reception when swing in the going stroke is finished.

The scanning controller 16a in the first embodiment controls such that the transducer elements performing ultrasound transmission/reception are sequentially shifted from the left end to the right end also in the returning stroke in the swing direction, as illustrated in the lower diagram of FIG. 5. Here, the scanning controller 16a controls such that the transducer element at the left end performs ultrasound transmission/reception when swing in the returning stroke is started and the transducer element at the right end performs ultrasound transmission/reception when swing in the returning stroke is finished.

With such control, the ultrasound probe 1 can perform two dimensional scanning of two intersecting cross sections in one-time reciprocating swing.

Here, the scanning controller 16a in the first embodiment controls a swing speed of the transducer elements depending on a time required for scanning each of cross sections once. In the two cross section scanning exemplified in FIG. 5, the scanning controller 16a needs to control scanning speed and the swing speed so that the scanning of one of two cross sections is finished during the one-time swing of the transducer element array 1a. Assuming that the time required for the one-time swing is "T", an ultrasound image generated by scanning in the going stroke is newly generated every "2T", and an ultrasound image generated by scanning in the returning stroke is newly generated every "2T". That is, in the two cross section scanning exemplified in FIG. 5, the swing speed is "1/T", and the frame rate is "½T". Thus, the scanning controller 16a controls such that the swing speed is substantially twice the frame rate. The scanning controller 16a determines the value of "T" based on the range of the frame rate allowed for observation of the operator while moving the ultrasound probe 1, and the shortest time required for the one-time swing of the ultrasound probe 1.

Moreover, the scanning controller 16a in the first embodiment controls the positions of the transducer elements performing ultrasound transmission/reception such that each of cross sections becomes a plane, based on a curvature in the swing direction of the transducer elements and a curvature in the arrangement direction of the transducer elements. As described with reference to FIGS. 3 and 4, the space scanned three-dimensionally by the ultrasound probe 1 can have various shapes depending on the curvature in the swing direction and the curvature in the arrangement direction.

Here, the transducer elements performing ultrasound transmission/reception are shifted with the same interval at certain time intervals, the shape of the scanned cross section becomes curved surface because of the curvature in the swing direction and the curvature in the arrangement direction. However, the scanned cross section for observation is preferable to be a plane. Thus, the scanning controller 16a in the first embodiment acquires position information on a sequence of intersection points (refer to dotted lines in the left diagram of FIG. 6) between the two intersecting planes and a curved surface on which the transducer element array 1a moves in association with swing, as illustrated in the left diagram of FIG. 6. The curved surface illustrated in the left diagram of FIG. 6 is a diagram when viewed from the above the contact face, and is actually a dome-formed curved surface. The scanning controller 16a extends the dome-formed curved surface to a plane so that the respective transducer element arrays are arranged linearly to acquire the position information of the sequence of the intersection points (refer to dotted lines in the right diagram of FIG. 6) after the extension, as illustrated in the right diagram of FIG. 6. Here, the transducer elements performing ultrasound transmission/reception are shifted with the same interval along the curved sequence of points illustrated in the right diagram of FIG. 6, whereby a plane is scanned. The scanning controller 16a projects points set with the same interval along the curved dotted lines illustrated in the right diagram of FIG. 6, in the arrangement direction.

Thus, the scanning controller 16a acquires the positions of the transducer elements with which each of two sections to be scanned in the going stroke and the returning stroke of swing becomes a plane, as illustrated in FIG. 7. In the case exemplified in FIG. 7, in the going stroke and the returning stroke, the transducer elements performing ultrasound transmission/reception are shifted from the left side to the right side at a certain time interval. In addition, in the case exemplified in FIG. 7, the intervals between transducer elements performing ultrasound transmission/reception are smaller at the right and left ends, and are larger at the center portion.

In the first embodiment, the scanning controller 16a may perform the position control additionally using information on the swing speed that is increased in the start of swing and decreased in the end of swing. In the first embodiment, the scanning controller 16a may not perform the above-described position control, but perform control so that each of cross sections becomes a curved surface having any desired curvature.

Figure 8:
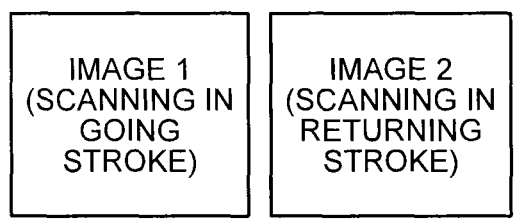
FIG. 8 is a diagram for explaining a display controller in the first embodiment.

Returning to FIG. 1, the display controller 16b in the first embodiment controls such that the ultrasound images based on ultrasound scanning performed on the cross sections are displayed on the monitor 2. FIG. 8 is a diagram for explaining the display controller in the first embodiment. For example, the display controller 16b in the first embodiment displays laterally an "image 1" that is an ultrasound image generated by the image generating unit 14 based on the reflected wave data generated by scanning in the going stroke, and an "image 2" that is an ultrasound image generated by the image generating unit 14 based on the reflected wave data generated by scanning in the returning stroke, as illustrated in FIG. 8.

Figure 9:
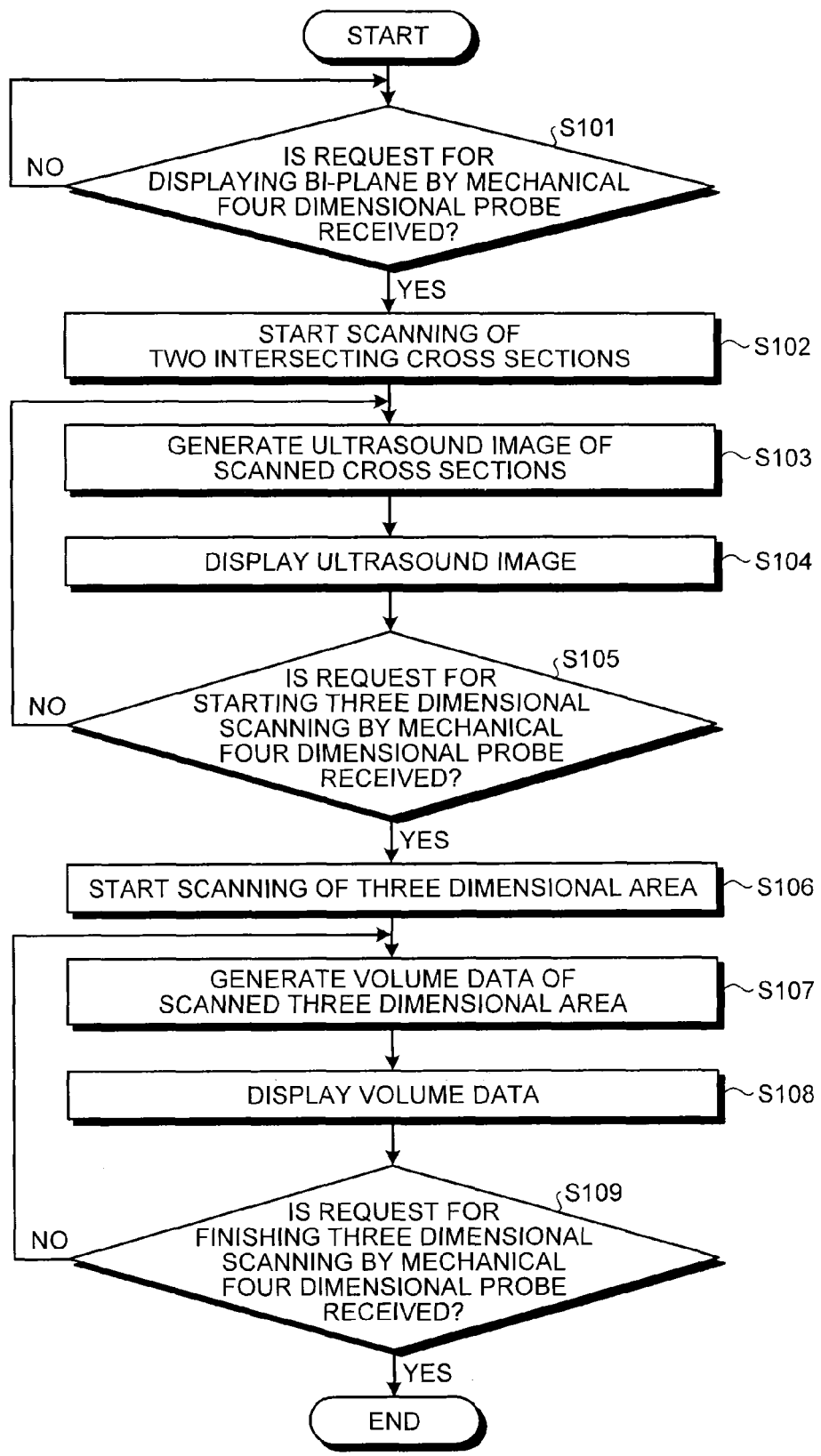
FIG. 9 is a flowchart of an example of processing of the ultrasound diagnosis apparatus in the first embodiment.

Next, the processing of the ultrasound diagnosis apparatus in the first embodiment is described with reference to FIG. 9. FIG. 9 is a flowchart of an example of processing of the ultrasound diagnosis apparatus in the first embodiment. The following description exemplifies a case where a display request of intersecting two cross sections (bi-plane) is received from the operator.

As illustrated in FIG. 9, the ultrasound diagnosis apparatus in the first embodiment determines whether a request for bi-plane display with the mechanical four dimensional probe (ultrasound probe 1) is received (Step S101). If the bi-plane display request is not received (No at Step S101), the ultrasound diagnosis apparatus waits until a display request is received.

If the bi-plane display request is received (Yes at Step S101), the ultrasound probe 1 starts scanning of intersecting two cross sections under the control of the transmitting/receiving unit 11 through the scanning controller 16a (Step S102). For example, the scanning controller 16a in the first embodiment controls such that one plane is scanned in the going stroke of swing and the other plane crossing the plane scanned in the going stroke is scanned in the returning stroke of swing by the scanning control described with reference to FIGS. 5 to 7.

Then, the image generating unit 14 generates the ultrasound images of the scanned cross sections (Step S103), and the monitor 2 displays the ultrasound images under the control of the display controller 16b (Step S104).

The scanning controller 16a determines whether a request for staring three dimensional scanning with the mechanical four dimensional probe (ultrasound probe 1) is received from the operator (Step S105). If the request for staring three dimensional scanning is not received (No at Step S105), the scanning of two cross sections with the ultrasound probe 1 is continued under the control of the scanning controller 16a, so that the image generating processing at Step S103 is performed.

If the request for staring three dimensional scanning is received from the operator who has referred to laterally displayed two ultrasound images and determined that a region to be observed is included in the scanned area (Yes at S105), the ultrasound probe 1 starts scanning of a three dimensional area (Step S106) under the control of the scanning controller 16a, so that the image generating unit 14 generates volume data of the scanned three dimensional area (Step S107). Then, the monitor 2 displays the volume data (Step S108) under the control of the display controller 16b. The volume data displayed at Step S108 is actually an MPR image or a volume rendering image generated by the image generating unit 14 based on the volume data.

Then, the scanning controller 16a determines whether a request for finishing three dimensional scanning with the mechanical four dimensional probe (ultrasound probe 1) is received from the operator (Step S109). If the request for finishing three dimensional scanning is not received (No at Step S109), the three dimensional scanning with the ultrasound probe 1 is continued under the control of the scanning controller 16a, so that the volume data generation processing at Step S107 is performed.

If the request for finishing three dimensional scanning is received (Yes at Step S109), the controller 16 finishes the control of ultrasound transmission.

As described above, in the first embodiment, only the intersecting cross sections to be used for display are scanned in the three dimensional space that can be scanned with ultrasound with the ultrasound probe 1. To be more specific, in the first embodiment, only the intersecting cross sections that are not parallel to the arrangement direction of the transducer element array 1a are scanned in the three dimensional space that can be scanned with ultrasound with the ultrasound probe 1. In this manner, the frame rate can be increased in the first embodiment, as compared with the case where the entire three dimensional space is scanned.

Here, the acoustic scanning by the ultrasound probe 1 can be performed at a speed several times higher than the mechanical swing speed. That is, it is only necessary, in the first embodiment, that one cross section is scanned once during a time "T", which enables higher density of ultrasound beams transmitted from the ultrasound probe 1. That is, the scanning in the going stroke and the scanning in the returning stroke can be performed at high spatial resolution and, consequently, the image quality of the ultrasound image can be improved. Therefore it is possible, in the first embodiment, to display a high quality image for determining whether a region to be observed is included in a three dimensional area scanned by the mechanical four dimensional probe at a high frame rate.

Figure 10:
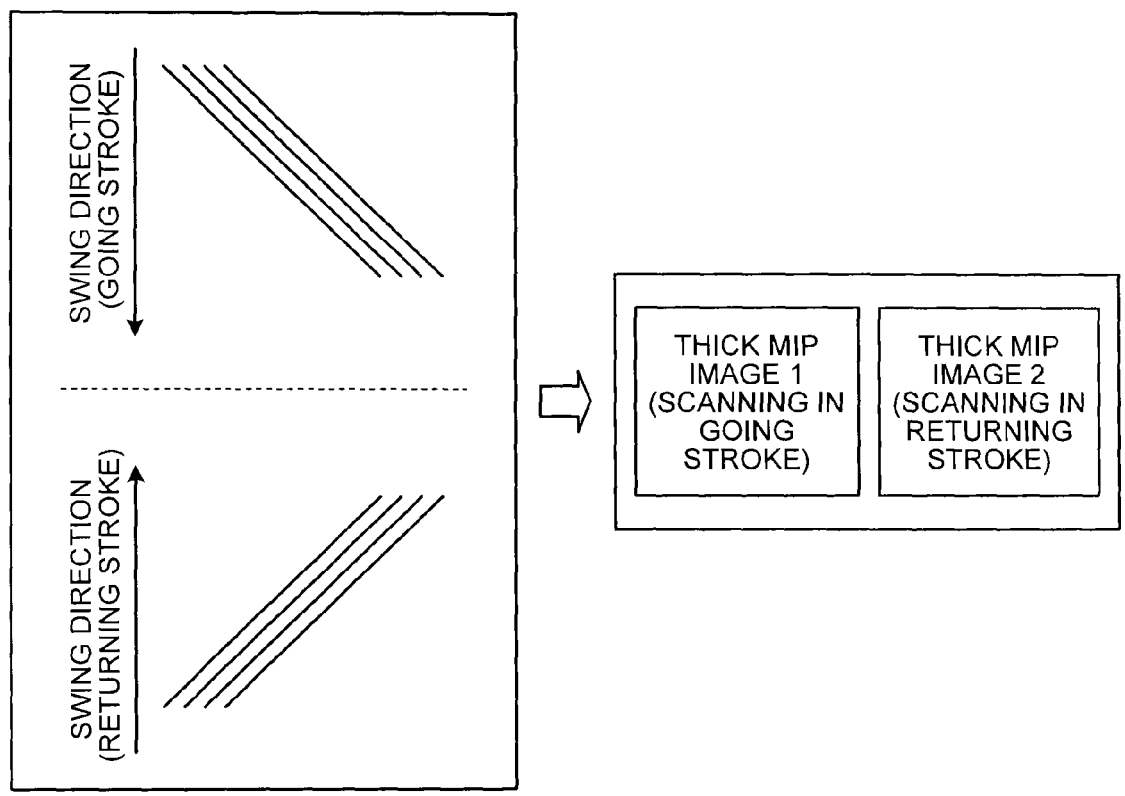
FIG. 10 is a diagram for explaining a modification of the first embodiment.

In the first embodiment in which only a plurality of cross sections are scanned, acoustic scanning can be performed having a time margin. Thus, it is possible to scan three or more cross sections. FIG. 10 is a diagram for explaining a modification of the first embodiment.

For example, when eight cross sections are scanned, the scanning controller 16a controls such that four sections that are not parallel to the arrangement direction of the transducer element array 1a and are parallel to one another are scanned in the going stroke in the swing direction. For example, the scanning controller 16a controls such that the ultrasound transmission/reception is sequentially performed from four transducer elements, which are positioned at the left end of the transducer element array 1a and each of which is set at the left end of a scanning line array of each cross section. Then, the scanning controller 16a sequentially shifts the four transducer elements performing ultrasound transmission/reception rightward while four-time ultrasound reception/transmission is repeated. In this manner, the scanning controller 16a controls the ultrasound probe 1 to scan four parallel cross sections in the going stroke. Moreover, the scanning controller 16 controls such that four cross sections that intersect the cross sections scanned in the going stroke in the swing direction and are parallel to one another are scanned in the returning stroke in the swing direction, as illustrated in FIG. 10. For example, the scanning controller 16a controls such that ultrasound transmission/reception similar to that in the going stroke is performed also in the returning stroke so as to scan the four parallel cross sections in the returning stroke.

Reflected data of the eight cross sections scanned under the control of the modification is displayed laterally as eight ultrasound images. Alternatively, in the modification, each of four pieces of the reflected wave data generated by scanning in the going stroke and four pieces of the reflected wave data generated by scanning in the returning stroke may be processed as three dimensional reflected wave data. That is, the image generating unit 14 may generate volume data of each of scanning in the going stroke and scanning in the returning stroke. In such a case, in the modification, the image generating unit 14 generates a thick maximum intensity projection (MIP) image, for example, based on each of volume data based on scanning in the going stroke and volume data based on scanning in the returning stroke. Then, the display controller 16b displays laterally a thick MIP image 1 based on scanning in the going stroke and a thick MIP image 2 based on scanning in the returning stroke, as exemplified in FIG. 10.

The above-described first embodiment exemplifies a case where the scanning for generating the image 1 is performed by scanning in the going stroke and the scanning for generating the image 2 is performed by scanning in the returning stroke. However, in the first embodiment, the scanning for generating the image 1 and a part of the image 2 may be performed by scanning in the going stroke, and the scanning for generating the rest of the image 2 may be performed by scanning in the returning stroke. Alternatively, in the first embodiment, the scanning for generating a part of the image 1 may be performed by scanning in the going stroke, and the scanning for generating the rest of the image 1 and the image 2 may be performed by scanning in the returning stroke.

A second embodiment exemplifies a case where the scanning controller 16a controls the positions of the transducer elements performing ultrasound transmission/reception so that all cross sections are scanned once in each of the going stroke and the returning stroke of swing.

The ultrasound diagnosis apparatus in the second embodiment has the same configuration as the ultrasound diagnosis apparatus in the first embodiment described with reference to FIG. 1. However, differently from the first embodiment, the scanning controller 16a in the second embodiment controls such that the scanning of all cross sections is performed once within the time of the one-time swing of the transducer element array 1a. That is, the scanning controller 16a controls the ultrasound probe 1 through the transmitting/receiving unit 11 to control such that the scanning of all cross sections is performed once within the time of the one-time swing of the transducer element array 1a.

For example, when two intersecting cross sections as a plurality of cross sections are scanned, the scanning controller 16a in the second embodiment performs, in the going stroke of swing, first scanning in a first shifting direction in which the transducer elements performing ultrasound transmission/reception are shifted from one end to the other end and second scanning in a second shifting direction opposite to the first direction alternately for each scanning line. Then, the scanning controller 16a in the second embodiment performs, in the returning stroke of swing, the first scanning and the second scanning that are alternately performed for each scanning line, in shifting directions opposite to those in the going stroke of swing.

Figure 11:
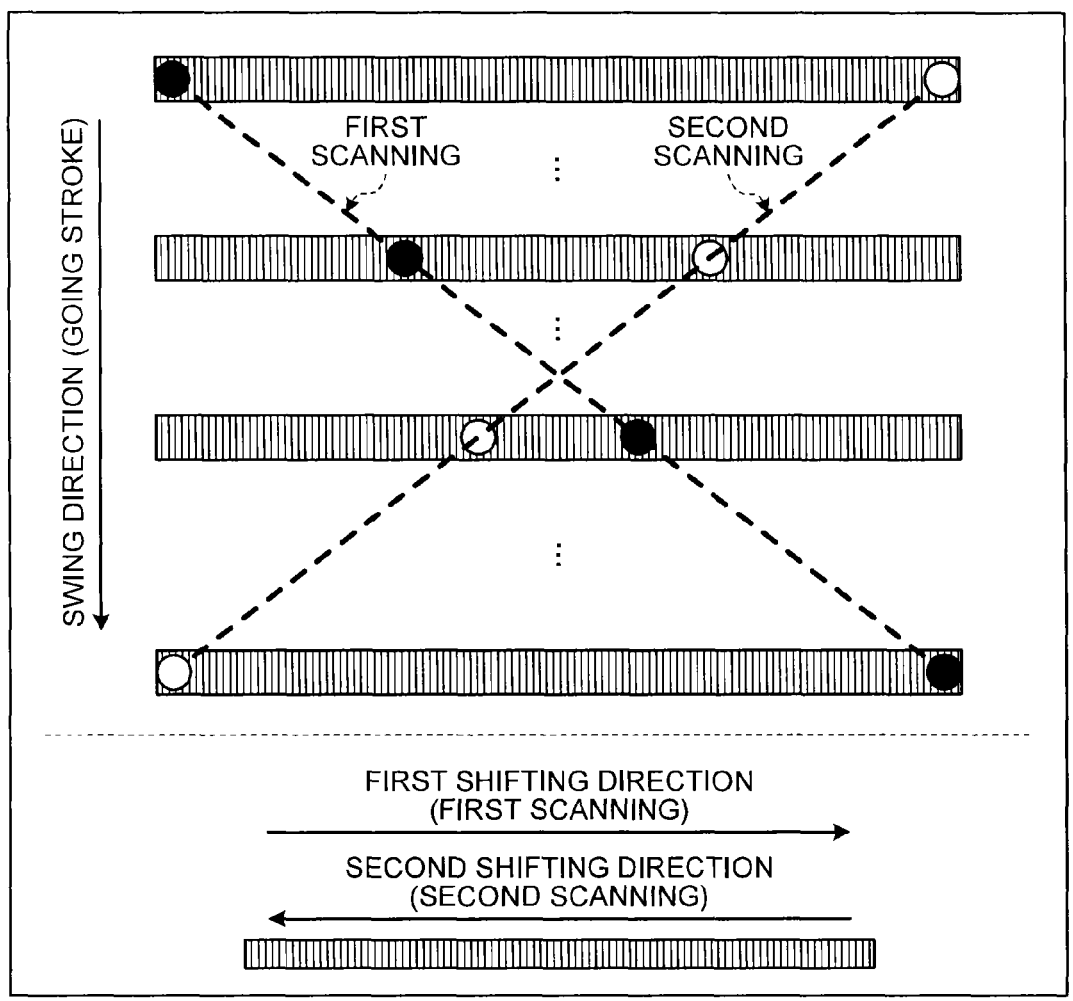
FIGS. 11, 12, 13A, and 13B are diagrams for explaining an example of scanning control by a scanning controller according to a second embodiment.
Figure 12:
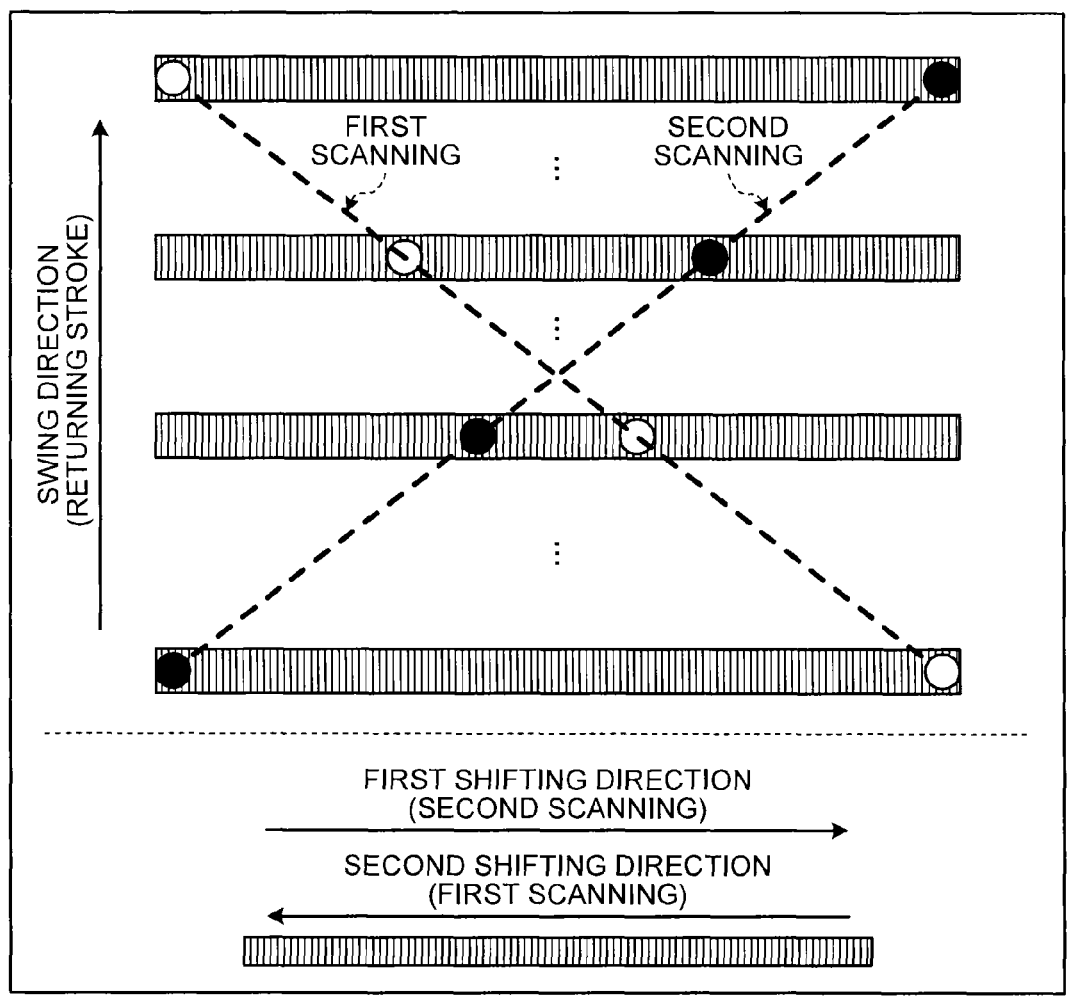

FIGS. 11, 12, 13A, and 13B are diagrams for explaining an example of scanning control by the scanning controller in the second embodiment. In FIGS. 11 and 12, respective positions of the swinging transducer element array 1a are illustrated in rectangular shapes when the ultrasound probe 1 is viewed from the above the contact face of the ultrasound probe 1 and the subject P, similarly to FIG. 5.

The scanning controller 16a in the second embodiment performs, in the going stroke in the swing direction, first scanning in the first shifting direction in which the transducer elements performing ultrasound transmission/reception are sequentially shifted from the left end to the right end and the second scanning in the second shifting direction in which the transducer elements performing ultrasound transmission/reception are sequentially shifted from the right end to the left end, alternately, as illustrated in FIG. 11. For example, the scanning controller 16a controls such that the first scanning illustrated by black filled circles and the second scanning illustrated by blank circles are performed alternately for each scanning line, as illustrated in FIG. 11.

Then, the scanning controller 16a in the second embodiment performs, in the returning stroke in the swing direction, the first scanning in the second shifting direction and the second scanning in the first shifting direction alternately, as illustrated in FIG. 12. For example, the scanning controller 16a controls such that the first scanning illustrated by blank circles and the second scanning illustrated by black filled circles are performed alternately for each scanning line, as illustrated in FIG. 12.

With such control, the ultrasound probe 1 can perform two dimensional scanning of two intersecting cross sections in the one-time swing.

The scanning controller 16a in the second embodiment controls the swing speed of the transducer elements depending on the time required for scanning each of cross sections once, similarly to the first embodiment. In the two section scanning exemplified in FIGS. 11 and 12, the scanning controller 16a needs to control such that the scanning of two sections is finished during the one-time swing of the transducer element array 1a. Here, assuming that the time required for the one-time swing is "T", an ultrasound image generated by the first scanning is newly generated every "T", and an ultrasound image generated by the second scanning is newly generated every "T". That is, in the two cross section scanning exemplified in FIGS. 11 and 12, the swing speed is "1/T", and the frame rate is "1/T". Thus, the scanning controller 16a controls such that the swing speed is substantially equal to the frame rate. The scanning controller 16a determines the value of "T" based on the range of the frame rate allowed for observation of the operator while moving the ultrasound probe 1, and the shortest time required for the one-time swing of the ultrasound probe 1.

Moreover, the scanning controller 16a in the second embodiment controls the positions of the transducer elements performing ultrasound transmission/reception so that each of cross sections becomes a plane, based on the curvature in the swing direction of the transducer elements and the curvature in the arrangement direction of the transducer elements, similarly to the first embodiment. That is, the scanning controller 16a controls, in the first shifting direction, such that the transducer elements performing ultrasound transmission/reception are shifted from the left side to the right side, and such that the intervals between transducer elements performing ultrasound transmission/ reception are smaller at the right and left ends, and are larger at the center portion, as exemplified in FIG. 13A.

Figure 13A:
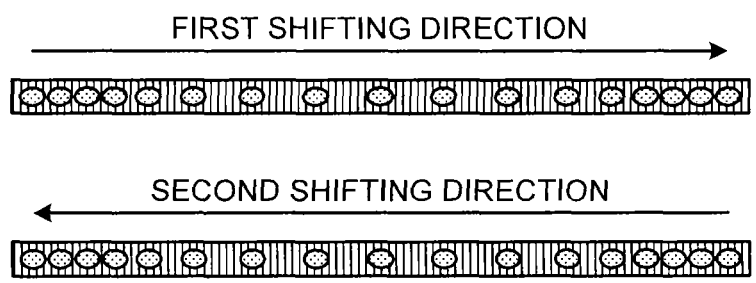

Moreover, the scanning controller 16a controls, in the second shifting direction, such that the transducer elements performing ultrasound transmission/reception are shifted from the right side to the left side, and such that the intervals between transducer elements performing ultrasound transmission/reception are smaller at the right and left ends, and are larger at the center portion, as exemplified in FIG. 13A, similarly to the case of the first shifting direction. In the case exemplified in FIG. 13A, the intervals between transducer elements performing ultrasound transmission/reception are same in the first and the second shifting directions.

In the second embodiment, the scanning controller 16a may perform the position control additionally using information on the swing speed that is increased in the start of swing and decreased in the end of swing. In the second embodiment, the scanning controller 16a may not perform the above-described position control, but perform control such that each of cross sections becomes a curved surface having any desired curvature.

Furthermore, in the two section scanning in the second embodiment, the scanning controller 16a controls such that ultrasound transmission/reception in the next swing starts from the transducer element having performed the last ultrasound transmission/reception in the former one-time swing, in order to prevent a case where the positions of both ends of the ultrasound image are misaligned among frames.

The above aspect is described in detail with reference to FIG. 13B. It is assumed that each of the first scanning and the second scanning is constituted by eight scanning lines, for example. Then, it is assumed that the first scanning in the first shifting direction is performed regarding "scanning lines 1, 3, 5, 7, 9, 11, 13, 15", and the second scanning in the second shifting direction is performed regarding "scanning lines 2, 4, 6, 8, 10, 12, 14, 16". It is also assumed that the scanning in the going stroke is performed in the order of the scanning lines 1 to 16. In such a case, the scanning in the going stroke is finished with scanning of the scanning line 16 in the second scanning, as illustrated in FIG. 13B.

Figure 13B:
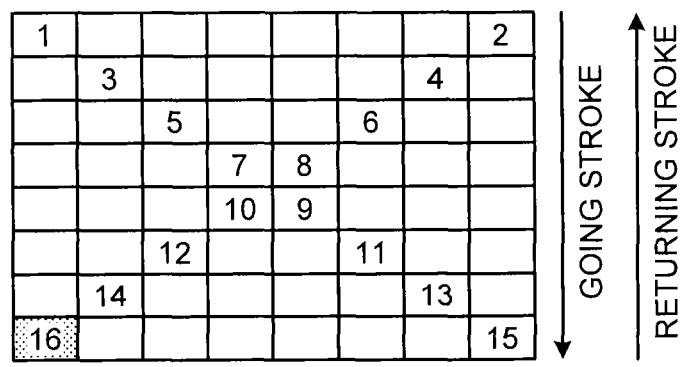

Thus, the scanning controller 16a controls such that the scanning in the returning stroke is started from the transducer element having performed scanning of the scanning line 16, as illustrated in FIG. 13B. Here, the second scanning in the first shifting direction is performed regarding the "scanning lines 16, 14, 12, 10, 8, 6, 4, 2" in the scanning in the returning stroke. Moreover, the first scanning in the second shifting direction is performed regarding the "scanning lines 15, 13, 11, 9, 7, 5, 3, 1" in the scanning in the returning stroke. That is, the scanning in the returning stroke is performed in the order of the scanning lines 16 to 1.

Figure 14:
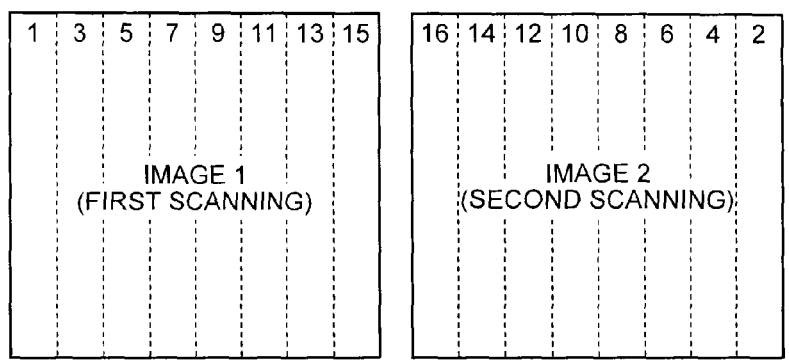
FIG. 14 is a diagram for explaining a display controller in the second embodiment.

Then, the display controller 16b in the second embodiment controls such that the monitor 2 displays a plurality of ultrasound images based on ultrasound scanning performed on the cross sections, similarly to the first embodiment. In the scanning control in the first embodiment, the reflected wave data sequentially collected in chronological order during swinging is collected in the order conforming to the scanning line arrays on the image. However, in the scanning control in the second embodiment, the reflected wave data sequentially collected in chronological order during swinging is not collected in the order conforming to the scanning line arrays on the image. Therefore the display controller 16b in the second embodiment controls such that each of a plurality of pieces of reflected wave data collected in chronological order during swinging is rearranged at a corresponding position in the respective cross sections depending on a scanning position. Then, the display controller 16b in the second embodiment controls such that a plurality of ultrasound images generated based on the rearranged reflected wave data are displayed on the monitor. FIG. 14 is a diagram for explaining the display controller in the second embodiment.

For example, the image generating unit 14 rearranges, under the control of the display controller 16b, the reflected wave data of the scanning lines 1 to 16 that is generated by the B-mode processor 12 in the scanning exemplified in FIG. 13B, in the manner as illustrated in FIG. 14. For example, the image generating unit 14 rearranges the reflected wave data in the order of the "scanning lines 1, 3, 5, 7, 9, 11, 13, 15" from the left side to the right side, as illustrated in FIG. 14, so as to generate the image 1 that is the ultrasound image based on the first scanning. The image generating unit 14 rearranges the reflected wave data in the order of the "scanning lines 16, 14, 12, 10, 8, 6, 4, 2" from the left side to the right side, as illustrated in FIG. 14, so as to generate the image 2 that is the ultrasound image based on the second scanning. In this manner, the monitor 2 displays the image 1 and the image 2 laterally under the control of the display controller 16b. Each of the image 1 and the image 2 is updated every time the time "T" passes.

The processing of the ultrasound diagnosis apparatus in the second embodiment is same as the ultrasound diagnosis apparatus in the first embodiment described with reference to FIG. 9, except for the following points. Thus, the overlapping description is omitted. That is, in the second embodiment, the scanning of two intersecting cross sections started at Step S102 is performed under the control described with reference to FIGS. 11 to 13B, etc. In the second embodiment, the reflected wave data is rearranged when an ultrasound image is generated at Step S103.

As describe above, in the second embodiment, only the intersecting cross sections to be used for display are scanned in the three dimensional space that can be scanned with ultrasound with the ultrasound probe 1, similarly to the first embodiment. Moreover, in the second embodiment, the first scanning and the second scanning are alternately performed during the one-time swing, and thus the frame rate can be twice as compared with the case of the first embodiment. Furthermore, it is only necessary, in the second embodiment, that each of two sections is scanned once during the time "T", which enables higher density of ultrasound beams transmitted from the ultrasound probe 1. Therefore it is possible, in the second embodiment, to display a high quality image for determining whether a region to be observed is included in the three dimensional area scanned by the mechanical four dimensional probe at a higher frame rate.

Figure 15:
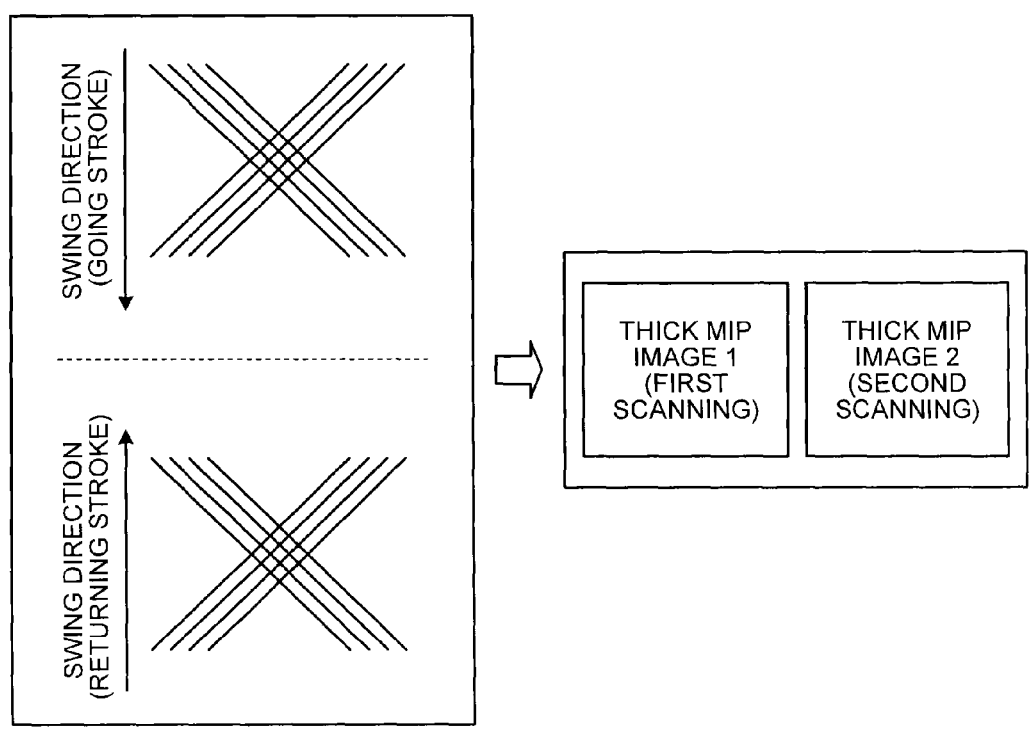
FIG. 15 is a diagram for explaining a modification of the second embodiment.

The acoustic scanning can be performed having a time margin also in the second embodiment. Thus, it is possible to scan three or more cross sections. FIG. 15 is a diagram for explaining a modification of the second embodiment.

For example, when eight cross sections are scanned, the scanning controller 16a controls such that four sections that are not parallel to the arrangement direction of the transducer element array 1a and are parallel to one another are scanned (first scanning of first cross section group), and four sections that intersect the first cross section group and are parallel to one another are scanned (second scanning of second cross section group), in both the going stroke and the returning stroke in the swing direction, as illustrated in FIG. 15. The scanning of the first cross section group in the going stroke is performed in the first shifting direction, while the scanning of the second cross section group in the going stroke is performed in the second shifting direction. The scanning of the first cross section group in the returning stroke is performed in the second shifting direction, while the scanning of the second cross section group in the returning stroke is performed in the first shifting direction.

Reflected data of the eight cross sections scanned under the control of the modification is rearranged depending on the scanning positions of the corresponding cross sections, and then displayed laterally as eight ultrasound images. Alternatively, in the modification, the image generating unit 14 may generate volume data corresponding to each of the first scanning and the second scanning, based on four pieces of reflected wave data generated in the first scanning of the first cross section group and four pieces of reflected wave data generated in the second scanning of the second cross section group that are processed respectively as three dimensional reflected wave data. In such a case, in the modification, the image generating unit 14 generates a thick MIP image, for example, based on each of volume data of the first scanning and volume data of the second scanning. Then, the display controller 16b displays laterally the thick MIP image 1 based on the first scanning and the thick MIP image 2 based on the second scanning, as illustrated in FIG. 15.

Figure 16A:
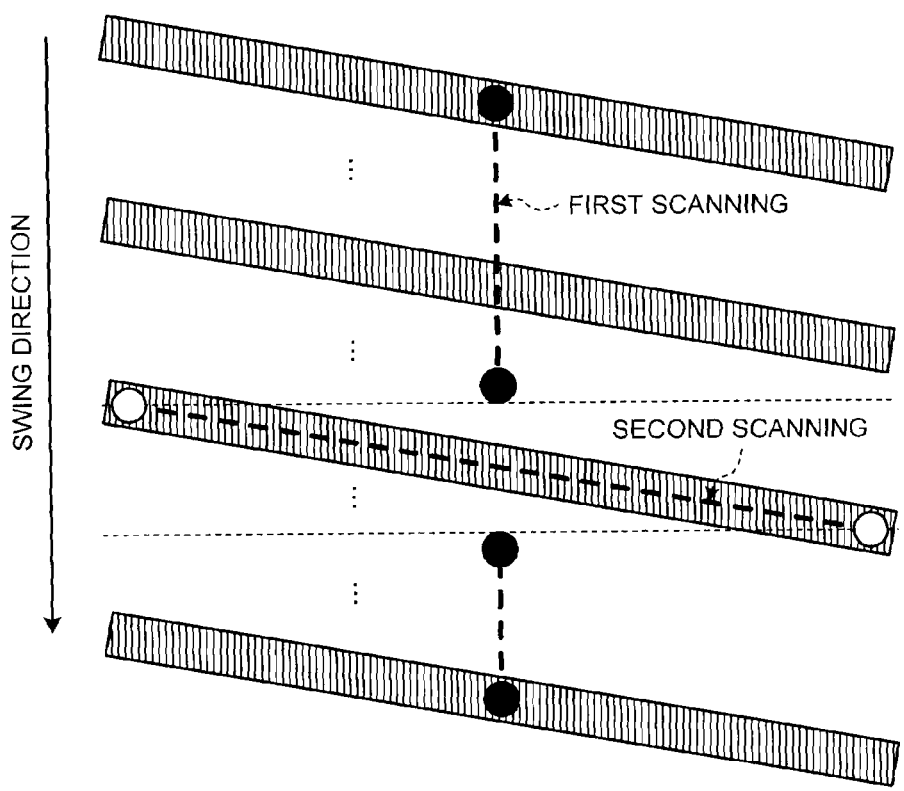
FIGS. 16A and 16B are diagrams for explaining an example of scanning control by a scanning controller according to a third embodiment.
Figure 16B:
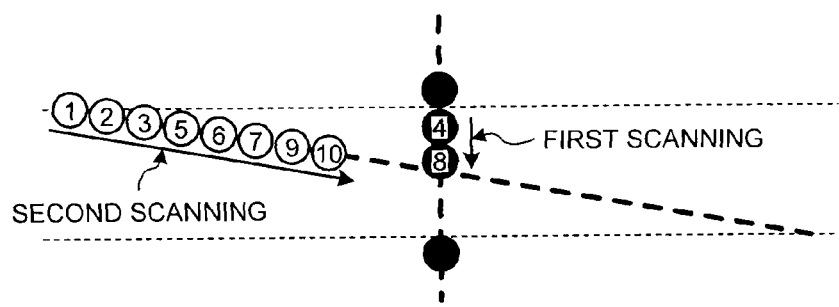

A third embodiment exemplifies a case where the scanning controller 16a controls, using a method different from that in the second embodiment, the positions of the transducer elements performing ultrasound transmission/reception so that all the cross sections are scanned once in each of the going stroke and the returning stroke of swing. The third embodiment is described with reference to FIGS. 16A and 16B. FIGS. 16A and 16B are diagrams for explaining an example of scanning control by the scanning controller in the third embodiment.

The ultrasound diagnosis apparatus in the third embodiment has the same configuration as the ultrasound diagnosis apparatus in the first embodiment described using FIG. 1. However, the scanning controller 16a in the third embodiment controls, using a method different from that described in the second embodiment, such that all the cross sections are scanned once within the time of the one-time swing of the transducer element array 1a.

For example, when two intersecting cross sections as the cross sections are scanned, for example, the scanning controller 16a in the third embodiment controls such that first scanning and second scanning are performed in the following process. That is, the scanning controller 16a in the third embodiment controls such that a transducer element in a given position performs ultrasound transmission/reception as the first scanning while the transducer elements are swinging. The scanning controller 16a controls the ultrasound probe 1 through the transmitting/receiving unit 11 to perform the first scanning. In the example illustrated in FIG. 16A, the scanning controller 16a controls such that the transducer element positioned in the substantially center (see the black filled circle in FIG. 16A), among the transducer elements, performs the first scanning.

The scanning controller 16a in the third embodiment performs the second scanning in which the transducer elements sequentially perform ultrasound transmission/reception once the swing angle of the transducer elements becomes a given angle during swinging. The scanning controller 16a controls the ultrasound probe 1 through the transmitting/receiving unit 11 to perform the second scanning. The scanning controller 16a can acquire the swing angle from the transmitting/receiving unit 11 controlling swing directly. In an example illustrated in FIG. 16A, once the swing angle of the transducer elements become a given angle during swinging, the scanning controller 16a controls such that the second scanning in which the transducer elements sequentially performs transmission/reception from the left end to the right end is performed.

Here, when the first scanning is interrupted by the second scanning, a center portion in the lateral direction of the ultrasound image based on the first scanning is lost. Then, in the third embodiment, the scanning controller 16*a* further performs the following control in order to prevent such a loss. That is, the scanning controller 16*a* in the third embodiment performs the first scanning at a given time interval during the second scanning is performed. In an example illustrated in FIG. 16B, the scanning controller 16*a* controls such that the first scanning is performed once every three times the second scanning is performed.

Also in the third embodiment, the swing speed of the transducer elements is controlled depending on the time required for scanning each of cross sections once, similarly to the first and the second embodiments. In the two cross section scanning exemplified in FIGS. 16A and 16B, the scanning controller 16*a* needs to control such that the scanning of two cross sections is finished during the one-time swing of the transducer element array 1*a*. Here, assuming that the time required for the one-time swing is "T", an ultrasound image generated by the first scanning is newly generated every "T", and an ultrasound image generated by the second scanning is newly generated every "T". That is, in the two cross section scanning exemplified in FIGS. 16A and 16B, the swing speed is "1/T", and the frame rate is "1/T". Thus, the scanning controller 16*a* controls such that the swing speed is substantially equal to the frame rate. The scanning controller 16*a* determines the value of "T" based on a range of the frame rate allowed for observation of the operator while moving the ultrasound probe 1, and the shortest time required for the one-time swing of the ultrasound probe 1.

Also in the third embodiment, the control based on the curvature in the swing direction and the curvature in the arrangement direction is performed so that the cross section of the second scanning becomes a plane, for example. Also in the third embodiment, similarly to the second embodiment, the display controller 16*b* controls such that the respective pieces of reflected wave data collected in chronological order during swinging are rearranged at the corresponding positions of the corresponding cross sections depending on the scanning positions. Then, also in the third embodiment, similarly to the second embodiment, the display controller 16*b* controls such that a plurality of ultrasound images generated based on the rearranged reflected wave data are displayed on the monitor.

The processing of the ultrasound diagnosis apparatus in the third embodiment is same as the ultrasound diagnosis apparatus in the first embodiment described with reference to FIG. 9 except for the following points. Thus, the overlapping description is omitted. That is, in the third embodiment, the scanning of two intersecting cross sections started at Step S102 is performed under the control described with reference to FIGS. 16A and 16B, etc. In the third embodiment, the reflected wave data is rearranged when an ultrasound image is generated at Step S103.

As described above, in the third embodiment, only the intersecting cross sections to be used for display are scanned in the three dimensional space that can be scanned with ultrasound with the ultrasound probe 1, similarly to the first and the second embodiments. Moreover, in the third embodiment, the first scanning in which the same transducer element performs ultrasound transmission/reception during swinging, and the second scanning in which the transducer elements performing ultrasound transmission/reception are shifted along the arrangement direction are performed, whereby the frame rate can be further improved. Moreover, it is only necessary, in the third embodiment, that each of two sections is scanned once during a time "T", which enables higher density of ultrasound beams transmitted from the ultrasound probe 1. Therefore it is possible, in the third embodiment, to display a high quality image for determining whether a region to be observed is included in the three dimensional area scanned by the mechanical four dimensional probe at a higher frame rate.

Also in the third embodiment, the acoustic scanning can be performed having a time margin. Thus, it is possible to scan three or more cross sections. In the third example, a plurality of transducer elements performing the first scanning may be set to perform a plurality of first scanning, for example. In the third example, a plurality of swing angles for the second scanning may be set to perform a plurality of second scanning, for example.

The above-described first to third embodiments exemplify a case where one part of cross sections is scanned in the three dimensional area that can be scanned in order to determine positions for three dimensional scanning with the ultrasound probe 1 that is the mechanical four dimensional probe. However, the ultrasound scanning control method described in the first to three embodiments may be also applied to a case where puncture operation is performed referring to the images collected by the ultrasound probe 1 that is the mechanical four dimensional probe.

Here, the bi-plane probe scanning intersecting two cross sections is used in puncture operation for determining whether a puncture needle is inserted to a region to be examined or treated, for example. Although the insertion of the puncture needle is also performed using the mechanical four dimensional probe or a two dimensional probe that is capable of three dimensional scanning, the frame rate is low in the three dimensional scanning. However, it is necessary to confirm an insertion position of the puncture needle in real time. In such a case, the mechanical four dimensional probe or the two dimensional probe may not be necessarily optimum as the ultrasound probe 1 for puncture.

The ultrasound probe 1 that is the mechanical four dimensional probe can be used as the bi-plane probe, for example, by performing the control processing described in the first to third embodiments. That is, when the control methods described in the first to third embodiments are employed, the ultrasound probe 1 that is the mechanical four dimensional probe can be also used for puncture operation.

In the following, a modification of the scanning control processing described in the first to third embodiments is described with reference to FIGS. 17 to 21. In the modification, the ultrasound probe 1 is provided with a puncture guide for inserting the puncture needle. FIGS. 17 to 21 are diagrams for explaining modifications of the first to third embodiments.

For example, the ultrasound probe 1 is provided with the puncture guide for inserting the puncture needle along any of cross sections. In other words, the puncture needle provided to the ultrasound probe 1 in the modifications is a product designed so that the insertion path of the puncture needle is included on any one of cross sections scanned by the ultrasound probe 1 under the control of the scanning controller 16*a*.

Figure 17:
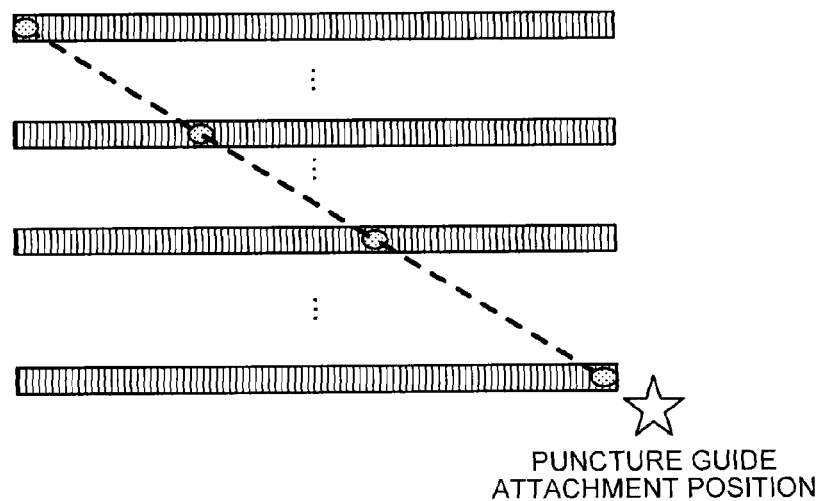
FIGS. 17, 18, 19, 20, and 21 are diagrams for explaining modifications of the first to third embodiments.

It is assumed, for example, that the puncture guide provided to the ultrasound probe 1 is a product appropriate for scanning in the going stroke and scanning in the returning stroke that are described in the first embodiment. It is also assumed that it is possible to select whether the puncture needle is inserted along a cross section scanned in the going stroke or along a cross section scanned in the returning stroke, depending on an attached position. In such a case, the puncture guide is provided to the ultrasound probe 1 so that the puncture needle is inserted along a cross section scanned by scanning in the going stroke, for example, as illustrated in FIG. 17. The puncture guide attachment position exemplified in FIG. 17 is also a position along a cross section scanned by the first scanning when the control method described in the second embodiment is employed.

Figure 18:
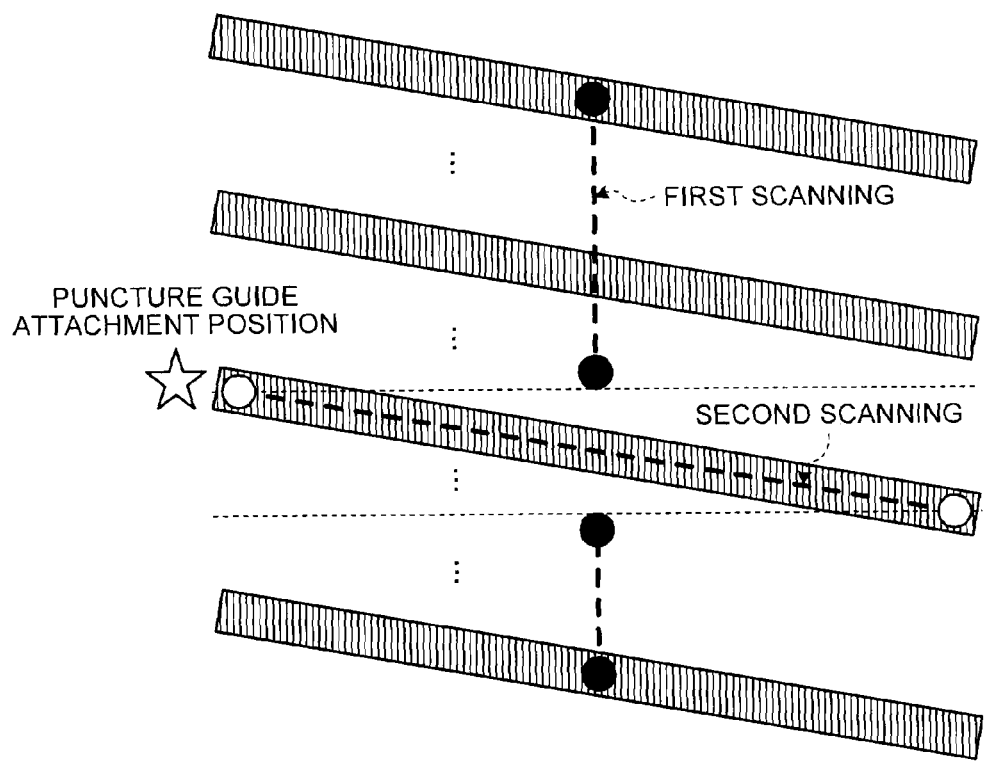

Alternatively, it is assumed, for example, that the puncture guide provided to the ultrasound probe 1 is a product appropriate for performing the first scanning and the second scanning that are described in the third embodiment. It is also assumed that it is possible to select whether the puncture needle is inserted along a cross section scanned in the first scanning or along a cross section scanned in the second scanning, depending on an attached position. In such a case, the puncture guide is provided to the ultrasound probe 1 so that the puncture needle is inserted along a cross section scanned in the second scanning, for example, as illustrated in FIG. 18.

Figure 19:
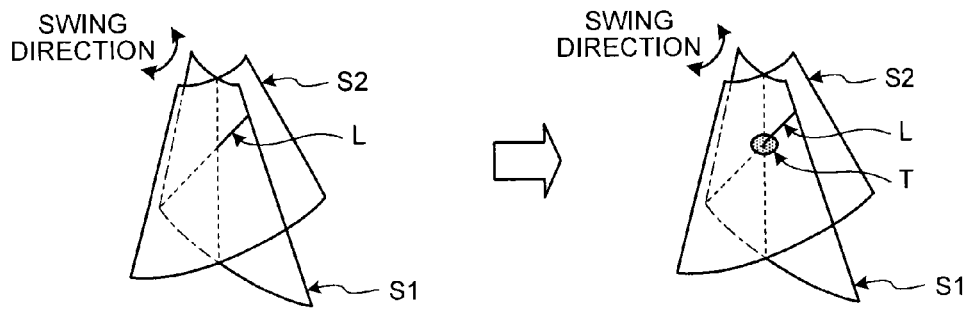
Figure 20:
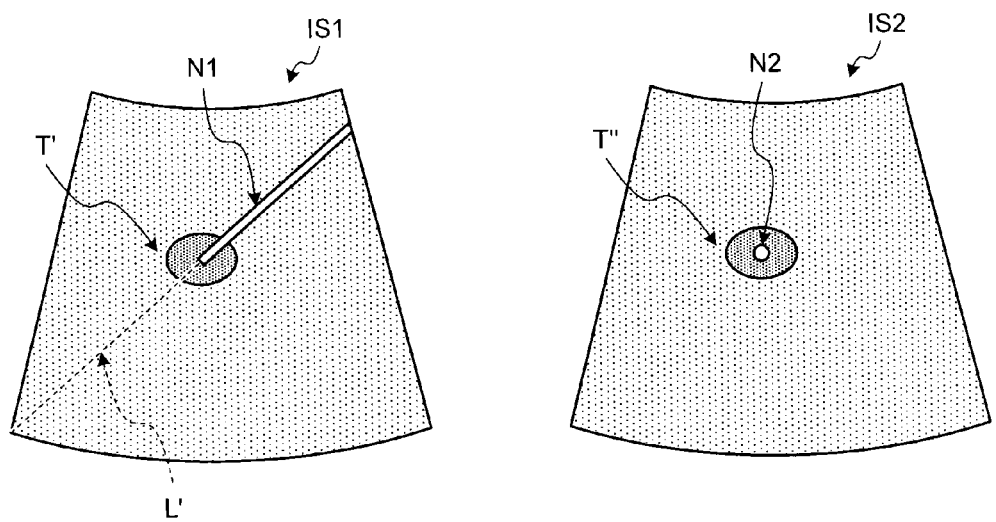

FIGS. 19 and 20 are diagrams exemplifying a case where the puncture guide is provided to the ultrasound probe 1 so that the insertion path of the puncture needle is included on a cross section scanned in the going stroke. A cross section S1 illustrated in FIG. 19 is a cross section scanned in the going stroke, while a cross section S2 illustrated in FIG. 19 is a cross section scanned in the returning stroke. When the puncture guide is provided to the ultrasound probe 1, an insertion path L of the puncture needle is included on the cross section S1, as illustrated in the left diagram of FIG. 19. The operator moves the ultrasound probe 1 in a state that the cross section S1 and the cross section S2 are scanned by swinging the transducer element array 1a along the swing direction. A region T illustrated in the right diagram of FIG. 19 is a region to be punctured. The operator fixes the ultrasound probe 1 at a position where the region T is scanned on both the cross section S1 and the cross section S2 and the insertion path L passes a center of the region T.

An image IS1 of FIG. 20 is an ultrasound image generated by scanning the cross section S1 and displayed. An image IS2 of FIG. 20 is an ultrasound image generated by scanning the cross section S2 and displayed. An area T' of FIG. 20 represents the region T visualized on the image IS1, while an area T'' of FIG. 20 represents the region T visualized on the image IS2. As illustrated in FIG. 20, an dotted line L' is superimposed on the image IS1, under the control of the display controller 16b. The dotted line L' is a guide line for puncture operation that is corresponding to the insertion path L. The display controller 16b estimates a position on the image IS1 that is corresponding to the insertion path L, based on an insertion direction of the puncture needle, which is defined depending on the specification of the puncture guide, and the attachment position of the puncture guide, and notifies the image generating unit 14 of the estimated position. The image generating unit 14 draws the dotted line L' at the position estimated by the display controller 16b on the image IS1.

The operator inserts the puncture needle until the end of a segment N1 reaches the center of the area T' while confirming that the high brightness segment N1 with the puncture needle as a reflection source is positioned on the dotted line L' superimposed on the image IS1. The operator confirms, referring to the image IS1 displayed on the monitor 2, that the end of the segment N1 is positioned in the center of the area T'. In addition, the operator confirms, referring to the image IS2 displayed on the monitor 2, that a high brightness point N2 with the puncture needle as a reflection source is positioned in the center of the area T''. The operator confirms, referring to the image IS1 and the image IS2, that the end of the puncture needle reaches the center of the region T. Thereafter, the operator collects tissue for pathological examination or performs radio frequency ablation (RFA).

As described above, it is possible to use the ultrasound probe 1 that is the mechanical four dimensional probe for puncture operation by performing the ultrasound scanning control methods described in the first to third embodiments.

The above-described modification can be applied when using a puncture guide designed so that the insertion path of the puncture needle is included on any one of scanning cross sections preliminarily set under the control of the scanning controller 16a. However, the insertion path of the puncture needle may not be included on any of scanning cross sections preliminarily set, depending on the kind of the puncture guide. That is, the above-described modification may not be applied if a commercial puncture guide is used.

Then, the scanning controller 16a may perform the following control processing. That is, the scanning controller 16a performs the scanning control of the ultrasound probe 1 so that one of cross sections includes the insertion path of the puncture needle that is defined by the puncture guide provided to the ultrasound probe 1. For example, the operator inputs, through the input device 3, the insertion direction of the puncture needle that is defined by the specification of the puncture guide and the attachment position of the puncture guide to the ultrasound probe 1. The scanning controller 16a acquires, based on such information, the position of the insertion path of the puncture needle in the three dimensional area that can be scanned three-dimensionally by swinging the transducer element array 1a. Then, the scanning controller 16a determines the position of a cross section that includes the insertion path of the puncture needle and can be scanned two-dimensionally by swinging the transducer element array 1a. Then, the scanning controller 16a calculates a parameter for scanning the determined cross section, and notifies the transmitting/receiving unit 11 of the calculated parameter.

Figure 21:
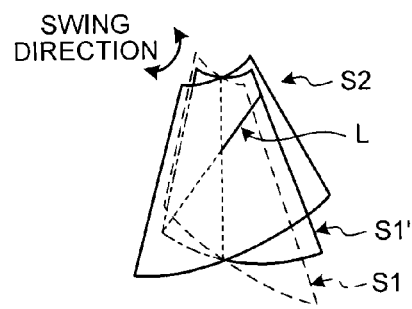

For example, the scanning controller 16a determines that the insertion path L of the puncture needle can be scanned on a cross section S1' adjacent to the cross section S1 scanned by scanning in the going stroke, as illustrated in FIG. 21. Referring to the upper diagram of FIG. 5, the cross section S1 is scanned while the transducer elements performing ultrasound transmission/reception are sequentially shifted from the left end to the right end in the going stroke in the swing direction. The left-end transducer element performs ultrasound transmission/reception when the going stroke of swing is started, and the right-end transducer element performs ultrasound transmission/reception when the going stroke of swing is finished, whereby the cross section S1 is scanned. The scanning controller 16a calculates a parameter for changing cross sections to which the going stroke scanning is subjected from the cross section S1 to the cross section S1'. Temporarily, the swing angle when the going stroke of swing is started is set to "−40°", and the swing angle when the going stroke of swing is finished is set to "+40°".

For example, the scanning controller 16a calculates the swing angle when ultrasound transmission/reception is started from the left-end transducer element to "−35°", based on a position of the section S1', and the scanning controller 16a calculates the swing angle when ultrasound transmission/reception is finished with the right-end transducer element to "+30°", based on the position of the section S1'. The scanning controller 16*a* calculates the positions of the transducer elements with which the cross section S1' becomes a plane by performing the same processing as the processing described using FIG. 6 and FIG. 7. Then, the scanning controller 16*a* notifies the transmitting/receiving unit 11 of the calculated parameter.

As a result, the ultrasound probe 1 starts ultrasound transmission/reception with the left-end transducer element once the swing angle of the transducer element array 1*a* becomes "−35°" after the going stroke of swing is started. Then, the ultrasound probe 1 finishes ultrasound transmission/reception with the right-end transducer element once the swing angle of the transducer element array 1*a* becomes "+30°" before the going stroke of swing is finished. In this manner, the ultrasound probe 1 scans, by scanning in the going stroke, the cross section S1' that is a plane including the insertion path L, as illustrated in FIG. 21. The scanning controller 16*a* may switch from the cross section S1 to the cross section S1' and change the position of the cross section S2 to be scanned in the returning stroke. For example, the scanning controller 16*a* may change the position of the cross section S2 to the position of a cross section making an angle, which is close to the right angles, with the cross section S1'.

With such scanning control, the ultrasound probe 1 that is the mechanical four dimensional probe can be used for puncture operation even if a commercial puncture guide is attached thereto. In the above-described two modifications, the scanning control for displaying thick MIP images, as described using FIGS. 10 and 15, etc., may be performed. In such a case, the thick MIP images are displayed, and thus the operator can perform puncture operation without losing the puncture needle even when the insertion path of the puncture needle deviates.

The above description exemplifies a case where the scanning controller 16*a* changes a cross section to be scanned depending on the insertion path of the puncture needle that is defined by the puncture guide provided to the ultrasound probe 1. However, when the ultrasound scanning control methods described in the first to third embodiments are performed, the scanning controller 16*a* may change the position of each cross section depending on a request from the operator, for example.

In the first to third embodiments, the illustrated components of each device are based on the functional concept, and are not necessarily configured physically as illustrated in the drawings. That is, the concrete form of the distribution and integration of the devices is not limited to the forms illustrated in the drawings, and the entire of the devices or one part thereof may be distributed/integrated functionally or physically in any desired unit, depending on various loads, a use state, etc. Moreover, the entire of processing functions performed by the devices or any one part thereof is achieved by a central processing unit (CPU) and a program analyzed and executed by the CPU, or achieved as hardware by wired logic.

The control methods described in the first to third embodiments are achieved by executing a preliminarily provided control program on a computer such as a personal computer and a workstation. The control program can be distributed through a network such as the Internet. The control program can be recorded in a computer readable recording medium such as a hard disk, a flexible disk (FD), a compact disk read only memory (CD-ROM), a magneto-optical disk (MO), and a digital versatile disk (DVD), and executed by the computer reading it out.

As described above, the first to third embodiments make it possible to display a high quality image for determining whether a region to be observed is included in a three dimensional area scanned by a mechanical four dimensional probe at a high frame rate.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus comprising:
   an ultrasound probe configured for three dimensional scanning by swinging a plurality of transducer elements in a swing direction orthogonal to an arrangement direction of the transducer elements;
   processing circuitry configured to
   cause the ultrasound probe to scan a first cross section in a going stroke of the swinging, the first cross section being not parallel to the swing direction and the arrangement direction,
   cause the ultrasound probe to scan a second cross section, intersecting the first cross section, in a returning stroke of the swinging, the second cross section being not parallel to the swing direction and the arrangement direction,
   generate a first ultrasound image of the first cross section based on outputs from the ultrasound probe in the going stroke,
   generate a second ultrasound image of the second cross section based on outputs from the ultrasound probe in the returning stroke, and
   cause a display to display the first ultrasound image and the second ultrasound image side by side.

2. The ultrasound diagnosis apparatus according to claim 1, wherein the processing circuitry is configured to control such that each of the first and second cross sections is scanned at least once during one-time reciprocating swing of the transducer elements.

3. The ultrasound diagnosis apparatus according to claim 1, wherein the processing circuitry is configured to control a swing speed of the transducer elements depending on a time required for scanning each of the first and second cross sections once.

4. The ultrasound diagnosis apparatus according to claim 1, wherein the processing circuitry is configured to control such that at least one of the first and second cross sections is scanned during one-time swing of the transducer elements.

5. The ultrasound diagnosis apparatus according to claim 4, wherein when two intersecting cross sections as the first and second cross sections are scanned, the processing circuitry is configured to shift the transducer elements performing ultrasound transmission/reception from one end to the other end in one-time swing, and to arrange a shifting direction of the transducer elements performing ultrasound transmission/reception to be the same in a going stroke and a returning stroke.

6. The ultrasound diagnosis apparatus according to claim 4, wherein the processing circuitry is further configured to control positions of the transducer elements performing ultrasound transmission/reception so that a plurality of cross sections are scanned once in each of a going stroke and a returning stroke of swing.

7. The ultrasound diagnosis apparatus according to claim 6, wherein when two intersecting cross sections as the first and second cross sections are scanned, the scanning controller performs, in the going stroke of swing, first scanning in a first shifting direction in which the transducer elements performing ultrasound transmission/reception are shifted from one end to the other end and second scanning in a second shifting direction opposite to the first shifting direction alternately for each scanning line, and in the returning stroke of swing, the first scanning and the second scanning that are alternately performed for each scanning line, in shifting directions opposite to those in the going stroke of swing.

8. The ultrasound diagnosis apparatus according to claim 7, wherein the processing circuitry is configured to control such that ultrasound transmission/reception in the next swing starts from the transducer element having performed the last ultrasound transmission/reception in the former one-time swing.

9. The ultrasound diagnosis apparatus according to claim 6, wherein when two intersecting cross sections as the first and second cross sections are scanned, the processing circuitry is configured to control first scanning in which a transducer element in a given position performs ultrasound transmission/reception while the transducer elements are swinging, and second scanning in which the transducer elements sequentially perform ultrasound transmission/reception once a swing angle of the transducer elements becomes a given angle during swinging, and control performance of the first scanning at a given time interval performing while the second scanning is performed.

10. The ultrasound diagnosis apparatus according to claim 6, wherein the processing circuitry controls such that each of a plurality of pieces of reflected wave data collected in chronological order during swinging is rearranged at a corresponding position in the respective cross sections depending on a scanning position to display a plurality of ultrasound images generated based on the rearranged reflected wave data on the given display.

11. The ultrasound diagnosis apparatus according to claim 1, wherein the processing circuitry is configured to control positions of the transducer elements performing ultrasound transmission/reception such that each of the first and second cross sections becomes a plane, based on a curvature in a swing direction of the transducer elements and a curvature in the arrangement direction of the transducer elements.

12. The ultrasound diagnosis apparatus according to claim 1, wherein the processing circuitry is configured to control such that each of the first and second cross sections becomes a curved surface having any desired curvature.

13. A control method comprising for an ultrasound probe capable of ultrasound three dimensional scanning by swinging a plurality of transducer elements in a direction orthogonal to an arrangement direction of the transducer elements, the control method comprising:

scanning a first cross section in a going stroke of the swinging, the first cross section being not parallel to the swing direction and the arrangement direction;

scanning a second cross section, intersecting the first cross section, in a returning stroke of the swinging, the second cross section being not parallel to the swing direction and the arrangement direction;

generating a first ultrasound image of the first cross section based on outputs from the ultrasound probe in the going stroke;

generating a second ultrasound image of the second cross section based on outputs from the ultrasound probe in the returning stroke; and causing a display to display the first ultrasound image and the second ultrasound image side by side.

\* \* \* \* \*